(12) United States Patent
Trojman

(10) Patent No.: US 11,908,570 B1
(45) Date of Patent: Feb. 20, 2024

(54) APPARATUS, SYSTEM AND METHOD FOR DATA DIFFUSION IN A MEDICAL COMPUTER SYSTEM

(71) Applicant: Allscripts Software, LLC, Chicago, IL (US)

(72) Inventor: Tomer Trojman, Beer Sheva (IL)

(73) Assignee: Allscripts Software, LLC, Chicago, IL (US)

( * ) Notice: Subject to any disclaimer, the term of this patent is extended or adjusted under 35 U.S.C. 154(b) by 0 days.

(21) Appl. No.: 16/460,441

(22) Filed: Jul. 2, 2019

Related U.S. Application Data

(63) Continuation-in-part of application No. 16/359,778, filed on Mar. 20, 2019.

(51) Int. Cl.
*G16H 40/20* (2018.01)
*G06N 7/02* (2006.01)
*G06F 16/22* (2019.01)

(52) U.S. Cl.
CPC ......... *G16H 40/20* (2018.01); *G06F 16/2246* (2019.01); *G06N 7/023* (2013.01)

(58) Field of Classification Search
CPC ..... G16H 40/20; G06F 16/2246; G06N 7/023
See application file for complete search history.

(56) References Cited

U.S. PATENT DOCUMENTS

| | | | | |
|---|---|---|---|---|
| 8,515,777 B1 * | 8/2013 | Rajasenan | ............... | G16H 50/30 705/7.14 |
| 8,585,607 B2 * | 11/2013 | Klap | ............... | A61B 5/113 600/534 |
| 10,483,003 B1 * | 11/2019 | McNair | ............... | G16H 50/20 |
| 10,535,429 B1 * | 1/2020 | Gravina | ............... | G16H 40/63 |
| 2007/0185739 A1 * | 8/2007 | Ober | ............... | G16H 50/20 600/301 |
| 2008/0065430 A1 * | 3/2008 | Rosow | ............... | G06Q 10/06 705/5 |
| 2010/0198755 A1 * | 8/2010 | Soll | ............... | G16H 10/60 706/11 |
| 2011/0125539 A1 * | 5/2011 | Bollapragada | ....... | G06Q 10/043 705/7.12 |
| 2012/0296675 A1 * | 11/2012 | Silverman | ............... | G16H 50/50 705/3 |

(Continued)

*Primary Examiner* — Jay M. Patel
(74) *Attorney, Agent, or Firm* — Peter Zura; LOZA & LOZA, LLP

(57) ABSTRACT

Technologies and techniques for operating a resource management system for medical software applications. Profile parameters of a first health care facility are received and processed to select one of a plurality stored profile data that contain profile parameters having a threshold similarity to the profile parameters for the first health care facility. A system resource manager loads resource management data associated with the selected profile data, wherein the resource management data comprises data relating to capabilities and capacities of the health care facility associated with the selected profile data. A systems intelligence manager performs predictive processing on the resource management data of the selected profile data to determine via simulation if the resource management data meets a threshold. The resource management data of the selected profile data is transmitted to the first health care facility for execution in the resource management software and updated using feedback data.

20 Claims, 10 Drawing Sheets

(56) References Cited

U.S. PATENT DOCUMENTS

| | | | | |
|---|---|---|---|---|
| 2013/0173281 A1* | 7/2013 | Rosow | ............... | G16H 40/63 |
| | | | | 705/2 |
| 2013/0304496 A1* | 11/2013 | Rangadass | ............ | G16H 20/70 |
| | | | | 705/2 |
| 2013/0304498 A1* | 11/2013 | Rangadass | ............ | G16H 40/20 |
| | | | | 705/2 |
| 2013/0304499 A1* | 11/2013 | Rangadass | ..... | G06Q 10/063114 |
| | | | | 705/2 |
| 2014/0195258 A1* | 7/2014 | Burton | ............... | G06Q 10/10 |
| | | | | 705/2 |
| 2014/0236630 A1* | 8/2014 | Murata | ............... | G16H 10/60 |
| | | | | 705/3 |
| 2015/0019259 A1* | 1/2015 | Qureshi | ............... | G16H 40/20 |
| | | | | 705/3 |
| 2015/0213223 A1* | 7/2015 | Amarasingham | ...... | G16H 50/30 |
| | | | | 705/2 |
| 2015/0370967 A1* | 12/2015 | Powell | ............... | G16H 50/20 |
| | | | | 705/2 |
| 2016/0042135 A1* | 2/2016 | Hogan | ............... | G16Z 99/00 |
| | | | | 705/2 |
| 2016/0371441 A1* | 12/2016 | Day | ............... | G16H 40/20 |
| 2018/0060521 A1* | 3/2018 | Connolly | ............ | G16H 15/00 |
| 2020/0057817 A1* | 2/2020 | Weber | ............ | G06N 5/01 |
| 2020/0155392 A1* | 5/2020 | Masuda | ............ | A61B 5/4561 |

* cited by examiner

APPARATUS, SYSTEM AND METHOD FOR DATA DIFFUSION IN A MEDICAL COMPUTER SYSTEM

RELATED APPLICATIONS

The present patent application is a continuation-in-part of U.S. patent application Ser. No. 16/359,778 to Tomer Trojman, titled "Apparatus, System and Method for Data Diffusion in a Medical Computer System," filed Mar. 20, 2019, the contents of which is incorporated by reference in its entirety herein.

FIELD OF TECHNOLOGY

The present disclosure is directed to technologies and techniques for processing medical data in a computer system. More specifically, the present disclosure is directed to artificial intelligence processing and related data diffusion in a medical computer system.

BACKGROUND

Emergency rooms are important in that they provide continuous access to healthcare. The lack of available hospital beds is a major difficulty in managing patient flow in emergency rooms (ERs). Typically, an ER patient flow competes against the flow of planned hospital admissions for the same beds, and the lack of clearly defined policy on either prioritizing ER patient flow over planned admissions or vice versa contributes in a disordered system.

Overcrowding has been described as the most serious problem and most avoidable cause of harm facing hospital systems. The American College of Emergency Physicians defines overcrowding as the situation when the identified need for emergency services exceeds available resources for patient care in the ED, hospital, or both. Another definition of overcrowding is the condition that exists when the demand for the emergency department services exceeds the available supply or there is an inability to move patients to inpatients area. Overcrowding due to poor patient flow increases the risk for patients, and is linked to increased mortality and reduces the capability of ED staff to anticipate surge pressures from adjacent emergency facilities.

Hospital beds are a scarce resource and therefore bed planning and allocation play an important role in the overall planning of hospital resources. When the accident & emergency department decides to admit a patient and if the allocated bed matches the specially required, then this considered an accepted case, and is labeled as "contained", as the patient is kept within the correct clinical specialty. If there is no available bed that matches the requested specialty at the point of demand then this is labeled as bed "overflow". Due to the increase of demand, bed management has become more critical. In addition, bed management has become an important criterion in delivering quality and cost effective health service.

Bed management is the allocation and provision of beds especially in a hospital where beds in specialists wards are a scarce resource. The bed occupancy rate (BOR) at the hospital and especially at the specialty level, changes due to the inherent variation of supply and demand by day of the week and time of the day. The decision to allocate an overflow bed, or to let the patient wait longer at emergency department, can be a complicated one. Policies may exist as guiding principles, such as "no waiting beyond 6 hour at Emergency department" rule. However, in practice, there are more factors to be considered, such as the extent of accident and emergency department crowding, projected demand and supply (for example, planned discharges).

Recently, medical software applications that involve bed management have begun to address the problems of bed overflow. These applications utilize aspects of artificial intelligence (AI) to determine and/or simulate various scenarios to determine areas of weakness within a system and to predict potential overflow occurrences. However, many of these applications require an extensive learning or training periods before the software is capable of functioning properly and/or optimally. During this training period, medical computer systems are often taxed from continuous data collection and latencies, and even data loss, may be introduced within the system.

Additionally, current medical software applications, particularly those operating on a computer network, do not adequately utilize the data of other, similarly-situated, computer software applications and/or their related operating environments, in order to collectively process data for improving AI data and application performance that is used by each respective computer system. There is a need in the art to provide greater crowdsourcing capabilities in medical software application systems.

SUMMARY

Various apparatus, systems and methods are disclosed herein relating to specialized computer systems for drug data processing.

In some illustrative embodiments, a resource management system for medical software applications is disclosed, comprising a processor; a memory, operatively coupled to the processor, wherein the memory is configured to store one or more profile data comprising profile parameters; a communications interface, operatively coupled to the processor, wherein the communications interface is configured to receive profile parameters of a first health care facility, configured to operate resource management software; a system profile manager, configured to process the received profile parameters for the first health care facility to select one of the one or more stored profile data that contain profile parameters having a threshold similarity to the profile parameters for the first health care facility; a system resource manager, configured to load resource management data associated with the selected profile data, wherein the resource management data comprises data relating to capabilities and capacities of the health care facility associated with the selected profile data; and a systems intelligence manager, configured to perform predictive processing on the resource management data of the selected profile data to determine via simulation if the resource management data meets a threshold, wherein the processor is configured to transmit the resource management data of the selected profile data to the first health care facility for execution in the resource management software, and wherein the systems intelligence manager is configured to receive feedback data via the communications interface and update the resource management data of the selected profile data, based on the feedback.

In some illustrative embodiments a method is disclosed for operating a resource management system for medical software applications, comprising: storing in a memory, one or more profile data comprising profile parameters; receiving, via a communications interface, profile parameters of a first health care facility, operating resource management software; processing, via a system profile manager, the received profile parameters for the first health care facility and selecting one of the one or more stored profile data containing profile parameters having a threshold similarity to the profile parameters for the first health care facility; loading, via a system resource manager, resource management data associated with the selected profile data, wherein the resource management data comprises data relating to capabilities and capacities of the health care facility associated with the selected profile data; performing, via a systems intelligence manager, predictive processing on the resource management data of the selected profile data to determine via simulation if the resource management data meets a threshold; and transmitting, via the communications interface, the resource management data of the selected profile data to the first health care facility for execution in the resource management software; receiving, via the communications interface, feedback data via the communications interface and updating, via the systems intelligence manager, the resource management data of the selected profile data, based on the feedback.

In some illustrative embodiments, a resource management system for medical software applications, comprising: a processor; a memory, operatively coupled to the processor, wherein the memory is configured to store one or more profile data comprising profile parameters; a communications interface, operatively coupled to the processor, wherein the communications interface is configured to receive profile parameters of a first health care facility, the health care facility being configured to operate resource management software on one or more cycles; a system profile manager, configured to process the received profile parameters for the first health care facility to select one of the one or more stored profile data that contain profile parameters having a threshold similarity to the profile parameters for the first health care facility; a system resource manager, configured to load resource management data associated with the selected profile data, wherein the resource management data comprises data relating to capabilities and capacities of the health care facility associated with the selected profile data; and a systems intelligence manager, configured to perform predictive processing on the resource management data of the selected profile data to determine via simulation if the resource management data meets a threshold, wherein the processor is configured to transmit the resource management data of the selected profile data to the first health care facility for execution in the resource management software prior to a resource management cycle.

BRIEF DESCRIPTION OF THE FIGURES

The present invention is illustrated by way of example and not limitation in the figures of the accompanying drawings, in which like references indicate similar elements and in which.

DETAILED DESCRIPTION

Various embodiments will be described herein below with reference to the accompanying drawings. In the following description, well-known functions or constructions are not described in detail since they may obscure the invention in unnecessary detail.

It will be understood that the structural and algorithmic embodiments as used herein does not limit the functionality to particular structures or algorithms, but may include any number of software and/or hardware components. In general, a computer program product in accordance with one embodiment comprises a tangible computer usable medium (e.g., hard drive, standard RAM, an optical disc, a USB drive, or the like) having computer-readable program code embodied therein, wherein the computer-readable program code is adapted to be executed by a processor (working in connection with an operating system) to implement one or more functions and methods as described below. In this regard, the program code may be implemented in any desired language, and may be implemented as machine code, assembly code, byte code, interpretable source code or the like (e.g., via C, C++, C #, Java, Actionscript, Swift, Objective-C, Javascript, CSS, XML, etc.). Furthermore, the term "information" as used herein is to be understood as meaning digital information and/or digital data, and that the term "information" and "data" are to be interpreted as synonymous.

In addition, while conventional hardware components may be utilized as a baseline for the apparatuses and systems disclosed herein, those skilled in the art will recognize that the programming techniques and hardware arrangements disclosed herein, embodied on tangible mediums, are configured to transform the conventional hardware components into new machines that operate more efficiently (e.g., providing greater and/or more robust data, while using less processing overhead and/or power consumption) and/or provide improved user workspaces and/or toolbars for human-machine interaction.

Figure 1:
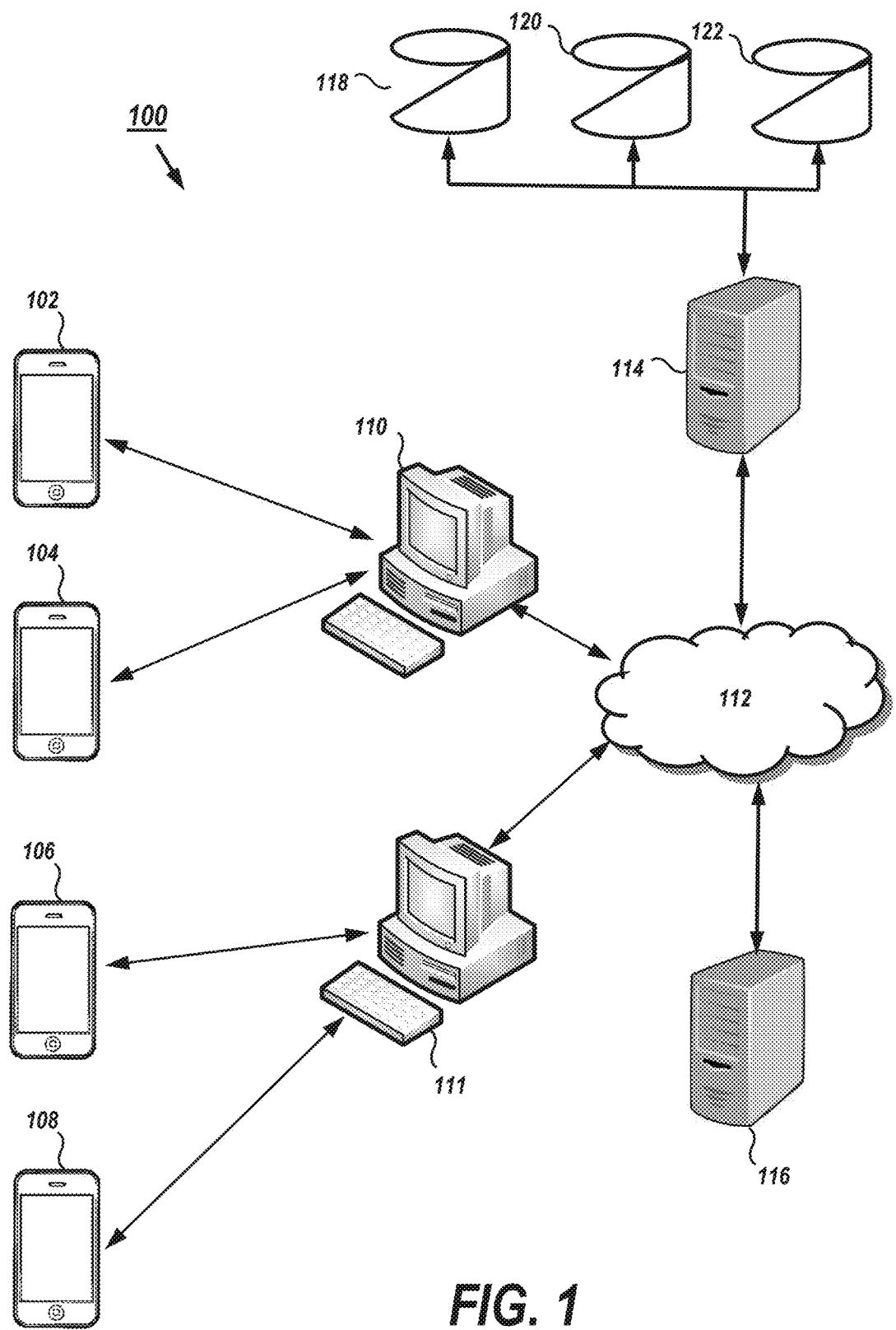
FIG. 1 illustrates a simplified overview of a processor-based computer system configured to perform resource processing and profile management under an illustrative embodiment.

Turning to FIG. 1, a system 100 is shown for resource processing and profile management in an illustrative embodiment. The system 100 may include a plurality of portable processing devices 102, 104, 106, 108 and associated computers and/or workstations 110, 111. Those skilled in the art understand that portable processing devices 102-108 and computers 110-111 may be configured as any suitable device that include, but are not limited to, cell phones, tablets, laptops, personal computers, workstations, medical processing devices, and the like. Portable processing devices 102-108 and computers 110-111 may communicate with each other via a direct wired or wireless connections (e.g., Bluetooth, Wifi), or through a local network (e.g., LAN).

In one example, portable processing devices 102, 104 may be communicatively coupled to computer 110 and portable processing devices 106, 108 may be communicatively coupled to computer 111. In this example, computers 110 and 111 may be computers from different networks and may be physically and/or geographically remote from one another. In another example, computers 110 and 111 may be computers from the same network in the same geographic region. Computers 110 and/or 111 may be communicatively coupled to a computer network 112, which is communicatively coupled to one or more of a plurality of servers 114, 116. In the example of FIG. 1, server 114 is communicatively coupled with a plurality of databases 118, 120, 122. The databases may be configured as large-scale databases suitable for use in systems, such as EMRs, EHRs, and the like. In some illustrative embodiments, the databases (118-122) may also include learning logic data for resource management and profile management data, discussed in greater detail below.

In some illustrative embodiments, system 100 is configured to receive resource management data from any and all devices 102-108, and/or computers 110 and 111. Generally speaking, the resource management data comprises data relating to capabilities and capacities of a health care facility. The resource management data may include, but is not limited to, patient demographics and related type(s) of medical specialty, date(s), times(s), the total number of inpatient beds, the daily capacity of inpatient beds for each specialty, the daily number of patients admitted into the Emergency Room (ER), grouped by the patient's demographics and the type of specialty, the number of patients that are moved into inpatient beds grouped by the type of specialty on a specific day, the number of patients discharged from the hospital grouped by the type of specialty on a specific day, and the maximum daily number of available beds matched to the type of specialty and patient demographic.

Additional resource management data may include, but is not limited to, a daily number of ER patient that have been moved to inpatient beds, grouped by patient demographic and related medical specialty type, the daily total number of patients admitted into the inpatient wards grouped by patient demographics and related medical specialty type, and the number of patients who stay in inpatient beds, including or not including newly admitted or recently discharged patients during the day, grouped by the type of specialty on a specific day, and the number of admitted ER patients that could not move into inpatient beds. The resource management data may also be provided resource values, such as bed priority, flexibility and availability indexes, control variables, grades, (e.g., ER admission grades, from low-to-high crowding set/cluster), residuals, and random and fixed effects and/or coefficient parameters.

As resource management data in provided, the computers 110, 111 (and/or devices 102-108) may forward the data to server 116, which may process the data to provide a resource model for optimizing the medical computer system 100. In some illustrative embodiments, the model processing may include a decision tree hierarchical structure comprising decision trees configured to analyze different levels of factors and through certain learning strategies, sort the data and variables into classes and provide intelligent rules. The intelligent grading rules may be configured to represent causing factors to the level of ER crowding, and achieve to reduce variables, further to solve correlation problem in a subsequent phase. In subsequent phases, the hierarchical relationship between the intelligent grading rules and the indexes of coping strategies may be used to construct a hierarchical linear model (HLM). Through the random effects estimates of model fitting, the result will intelligently detect the differences in the degree of strategic mechanisms among hospital medical computer systems utilizing the resource management software.

In some illustrative embodiments, an Agent-Based Model (ABM) may be used for server 116, utilizing rules governing the behavior of the individual agents that populate the system 100 via any of the devices 102-111. The system behavior may be configured to utilize local level actions and interactions provided by devices 102-108 and/or 108-110. This model may be configured to represent the complex dynamics found in an ER, representing each individual and system as an individual agent. Here, active and passive agents may be used, where active agents represent the devices (e.g., 102-108) associated with user involved in the ER (e.g., admission staff, nurses, doctors, etc.). Passive agents represent services and other reactive systems, such as the information technology (IT) infrastructure or services used for performing tests. Moore State machines may be used to represent the actions of each agent. This takes into consideration all the variables that are required to represent the many different states that such a user (e.g., patient, hospital staff) may be in throughout the course of their time in a hospital emergency department. The change in these variables, invoked by an input from an external source, may be modeled as a transition between states. In some specific cases, the state machine involves probabilistic transitions, where a given combination of current state and input has more than one possible next state. Which transition is made is chosen at random at the time of the transition, and weights on each transition may provide a means for specifying transitions that are more or less likely for a given individual.

In some illustrative embodiments, probabilities may be different for each agent. In this way heterogeneity is provided to agents as people, since agent behavior can be probabilistically defined external to their state. The communication between individuals is modeled as the inputs that agents receive and the outputs they produce, both implicitly and explicitly. The communication model for the system 100 may be configured under a plurality of types, where one type is 1-to-1 communication, such as between two devices (e.g., 104, 108), for instance admission staff and patient, where a message has a single source and a single destination, as well as between patients, or staff personnel. Another type may be a 1-to-n communication, where a message has a single source (e.g., 111) and a specific set of recipients (e.g., 106, 108), for example when a doctor communicates with both patient and his companion, or when doctor communicates with other doctors and nurses. Another type is 1-to-location communication, where a message has a single source (e.g., 116), but it is received by every agent within a certain area or location (e.g., 102-108). In some illustrative embodiments, the resource management models may utilize techniques such as Exhaustive Search, Monte Carlo and/or Pipeline (also known as "Assembly Line") statistical methods for processing resource data to produce predictive/intelligent data for the system 100.

In some illustrative embodiments, a fuzzy logic model may be used for the resource data processing for producing predictive/intelligence data. Unlike conventional (e.g., Boolean) logic, fuzzy logic allows for different gradations of conditional outputs (e.g., true, false, very true, approximately false, completely true, etc.). The combination of results in fuzzy rules and individual rules of assessment may be carried out using fuzzy cluster operations, where operations on fuzzy sets are different from operations on non-fuzzy sets. The results of each rule may be evaluated, and subsequently assembled to obtain a resultant. The fields which are derived from rules may be merged in different ways, using different operators for the merging process to obtain a final fuzzy output. The desired output may be located with certainty by using a defuzzification technique (e.g., Center of Gravity).

During operation, a hospital, ER facility or the like utilizing system 100 initially enters data, including resource management data described herein, into any of devices 110-111, prior to a first operation and/or operational cycle. Additionally, the resource management data may include an emergency department work index (EDWIN) score, and/or other related data. Of course, the resource management data may, alternately or in addition, be entered via any of devices 102-108 as well. Once the data is entered, it may be transmitted to server 116, which processes the resource management data and calculates optimal values using predictive/intelligence processing for the resource management software operating on device(s) 110 and/or 111. One or more devices 110, 111 executes resource management software, which in turn provides signals and/or data instructing users of system 100 to distribute and/or modify resources within a portion of a health car facility (e.g., ER facility). During the course of operation, users of the resource management software enter feedback data, for example, indicating if resources have been allocated relative to any aspect of the resource management data. As the feedback data is received in server 116, the server 116 may re-process the resource management data to determine if adjustments to the optimized values may be required. If so, the server provides the updated values to the devices (e.g., 110, 111), wherein the resource management software updates itself using the updated values and adjusts the signals and/or data provided to the system 100 to distribute and/or modify resources within the health care facility.

This process may be repeated until the server detects a minimum number of adjustments required for the resource allocation software. This minimum number may be predetermined by the system as a threshold, and is not required to be zero. Once the threshold is achieved, the server 116 may be configured to save all of the resource management data for the resource management software as a profile. This profile may subsequently be recalled by resource management software on device(s) 110, 111, where the profile automatically loads in the resource management data associated with the profile. Those skilled in the art will appreciate that the profile configuration may be customized under the present disclosure. For example, individual profiles may be configured for each day of the week, and for time periods for each day (e.g., morning, afternoon, evening, night), as discussed in greater detail below in connection with FIG. 6. Individual days may also be tagged as special days or holidays (e.g., New Year's Eve, St. Patrick's Day, sporting event, etc.), where a special profile may be created for times of that particular day. As the resource management software cycles from one period to another (e.g., evening to night, Monday to Tuesday, etc.), the system (e.g., via server 116) automatically cycles from one profile (or profile portion) to the next, saving each profile with updated feedback data.

It should also be understood by those skilled in the art that the resource management profiles may be used in the system 100 to "crowdsource" resource management data profiles from multiple, different health care facilities. Each profile may be associated with a health care facility profile that includes facility profile data that characterizes the facility. For example, the facility profile data may include geographic data that identifies a region and location of the facility, along with other descriptive data (e.g., large, urban city, rural town, high/low health care facility density, warm/cold climate, etc.). The facility profile data may also include generalized resource management data, describing staffing capabilities, equipment, etc. In an illustrative embodiment, the resource management software operating on the system 100 may be configured to receive facility profile data, wherein the server 116 may process the facility profile data to determine the most similar medical facilities matching the facility profile data. Once a most-similar match is found, the server 116 may load the resource management data profile for the match, and transmit the profile to the device (e.g., 110, 111) for use in the resource management software. In some illustrative embodiments, multiple profiles may be normalized or averaged together to create a composite profile for use in the system 100.

Figure 2:
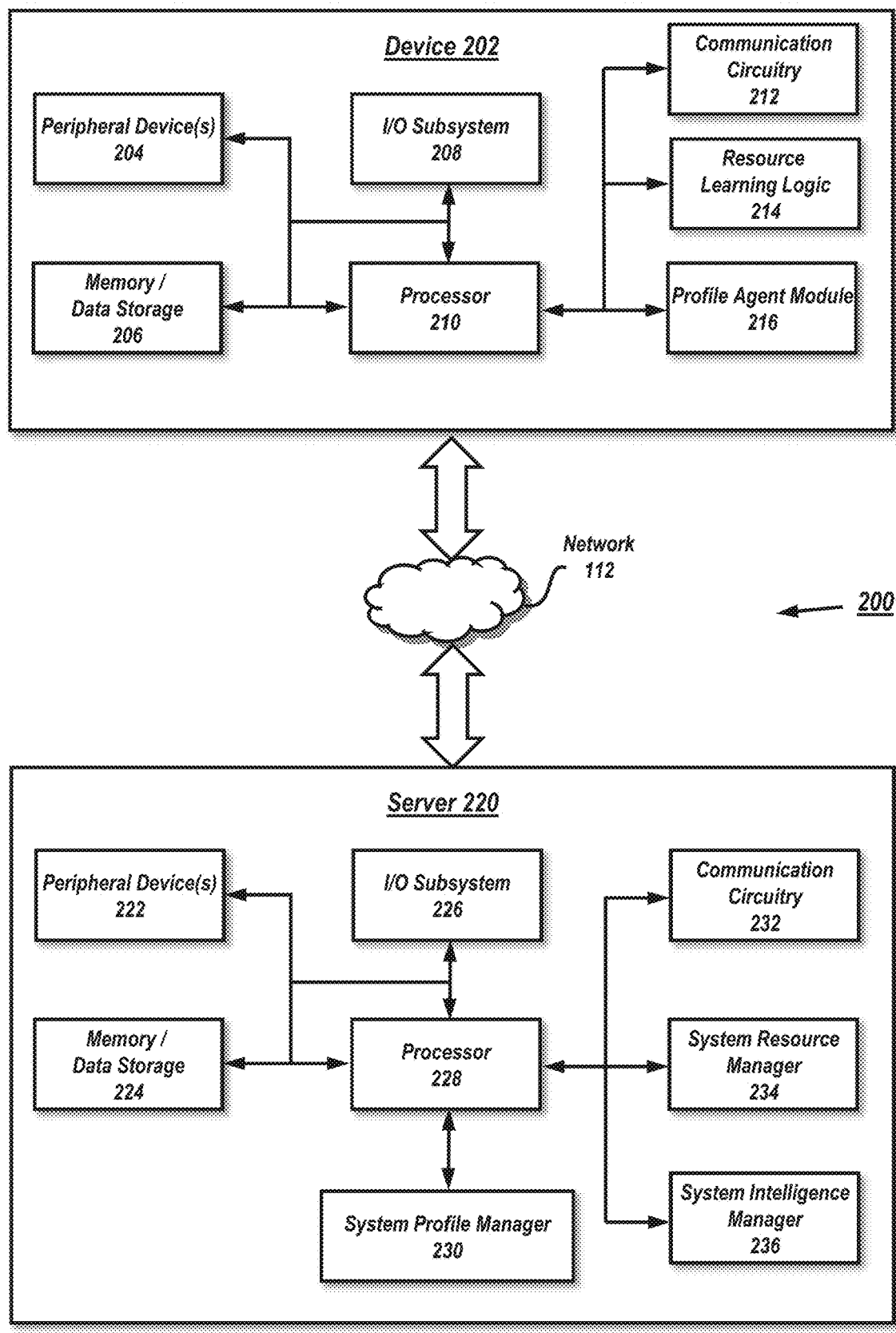
FIG. 2 shows an operating environment for a device and a server in a mobile agent environment for resource processing and profile management under an illustrative embodiment.

FIG. 2 shows an operating environment 200 for system 100 that includes a processing device 202, which may be configured as any of devices 102-108 and/or 110-111, and a server 220, which may be configured as server 114, 116, communicating via the network 112 wherein the operating environment is configured to process resource management data and profile data as described herein. In the illustrative embodiment, the processing device 202 includes a processor 210 or processor circuit, one or more peripheral devices 204, memory/data storage 206, communication circuitry 212, input/output (I/O) subsystem, a resource learning logic module and 214 and profile agent module 216.

The profile agent module 216 of environment 200 may be configured to perform functions pertaining to requesting, loading and/or executing resource management profiles and associated resource management data, as discussed herein. Resource learning logic module 214 may be configured to process and execute resource management data. Resource learning logic module 214 may also be configured to receive feedback data and perform predictive/intelligence processing on the data. In some illustrative embodiments, resource learning logic module may communicate with system intelligence manage 236 and/or system resource manager 234 of server 220, wherein the system intelligence manage 236 and/or system resource manager 234 perform predictive/intelligence processing on the resource management data and feedback data, and communicate the resultant data to resource learning logic module 214. In some illustrative embodiments, resource learning logic 214 and/or profile agent module 216 may be incorporated into memory/data storage 206 with or without a secure memory area, or may be a dedicated component, or incorporated into the processor 210. Of course, processing device 202 may include other or additional components, such as those commonly found in a digital apparatus and/or computer (e.g., sensors, various input/output devices), in other embodiments. Additionally, in some embodiments, one or more of the illustrative components may be incorporated in, or otherwise form a portion of, another component. For example, the memory/data storage 206, or portions thereof, may be incorporated in the processor 210 in some embodiments.

The processor 210 may be embodied as any type of processor currently known or developed in the future and capable of performing the functions described herein. For example, the processor 210 may be embodied as a single or multi-core processor(s), digital signal processor, microcontroller, or other processor or processing/controlling circuit. Similarly, memory/data storage 206 may be embodied as any type of volatile or non-volatile memory or data storage currently known or developed in the future and capable of performing the functions described herein. In operation, memory/data storage 206 may store various data and software used during operation of the processing device 210 such as access permissions, access parameter data, operating systems, applications, programs, libraries, and drivers.

Memory/data storage 206 may be communicatively coupled to the processor 210 via an I/O subsystem 208, which may be embodied as circuitry and/or components to facilitate input/output operations with the processor 210, memory/data storage 206, and other components of the processing device 202. For example, the I/O subsystem 208 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 208 may form a portion of a system-on-a-chip (SoC) and be incorporated, along with the processor 210, memory/data storage 206, and other components of the processing device 202, on a single integrated circuit chip.

The processing device 202 includes communication circuitry 212 (communication interface) that may include any number of devices and circuitry for enabling communications between processing device 202 and one or more other external electronic devices and/or systems. Similarly, peripheral devices 204 may include any number of additional input/output devices, interface devices, and/or other peripheral devices. The peripheral devices 204 may also include a display, along with associated graphics circuitry and, in some embodiments, may further include a keyboard, a mouse, audio processing circuitry (including, e.g., amplification circuitry and one or more speakers), and/or other input/output devices, interface devices, and/or peripheral devices.

The server 220 may be embodied as any suitable server (e.g., a web server, etc.) or similar computing device capable of performing the functions described herein. In the illustrative embodiment of FIG. 2 the server 220 includes a processor 228, an I/O subsystem 226, a memory/data storage 224, communication circuitry 232, and one or more peripheral devices 222. Components of the server 220 may be similar to the corresponding components of the processing device 202, the description of which is applicable to the corresponding components of server 220 and is not repeated herein for the purposes of brevity.

The communication circuitry 232 of the server 220 may include any number of devices and circuitry for enabling communications between the server 220 and the processing device 202. In some embodiments, the server 220 may also include one or more peripheral devices 222. Such peripheral devices 222 may include any number of additional input/output devices, interface devices, and/or other peripheral devices commonly associated with a server or computing device. In some illustrative embodiments, the server 220 also includes system profile manager 230, system resource manager 234 and system intelligence manager 236. System profile manager 230 may be configured to manage some or all of the facility profiles, including the associated resource management data by storing, modifying and transmitting profiles to devices (e.g., 202). System resource manager 234 may be configured to process the resource data received from devices (e.g., 202) and apply predictive/intelligent processing to the data. Specific predictive/intelligent algorithms may be provided by systems intelligence manager 236 that is communicatively coupled to system resource manager 234.

During operation, the environment 200 allows the system 100 to manage and process resource management data to allow a health care facility to manage resources using predictive/intelligent data. Using feedback provided by devices (e.g., 102-108), the environment can update the predictive/intelligent data to reflect real-time changes in facility operations and update the resource management data. By using a profile management system as disclosed herein, the environment 200 may allow the system 100 to store profiles that are specific to health care facilities and the circumstances in which they operate and manage resource. By allowing the profiles to be stored, modified, updated and/or recalled, health care facilities may quickly retrieve the resource management data without requiring the resource management software to continuously operate under a learning mode. Similarly, one health care facility can effectively utilize the data of another similarly-situated health facility without having to initiate a learning procedure at all. Those skilled in the art will appreciate that the configurations disclosed herein provide improved technical solutions to conventional medical data systems to provide improved systems operations.

Continuing with the illustrated embodiment of FIG. 2, communication between the server 220 and the processing device 202 takes place via the network 112 that may be operatively coupled to one or more network switches (not shown). In one embodiment, the network 112 may represent a wired and/or wireless network and may be or include, for example, a local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web). Generally, the communication circuitry of processing device 202 and the communication circuitry 232 of the server 220 may be configured to use any one or more, or combination, of communication protocols to communicate with each other such as, for example, a wired network communication protocol (e.g., TCP/IP), a wireless network communication protocol (e.g., Wi-Fi, WiMAX), a cellular communication protocol (e.g., Wideband Code Division Multiple Access (W-CDMA)), and/or other communication protocols. As such, the network 112 may include any number of additional devices, such as additional computers, routers, and switches, to facilitate communications between the processing device 202 and the server 220.

Figure 3:
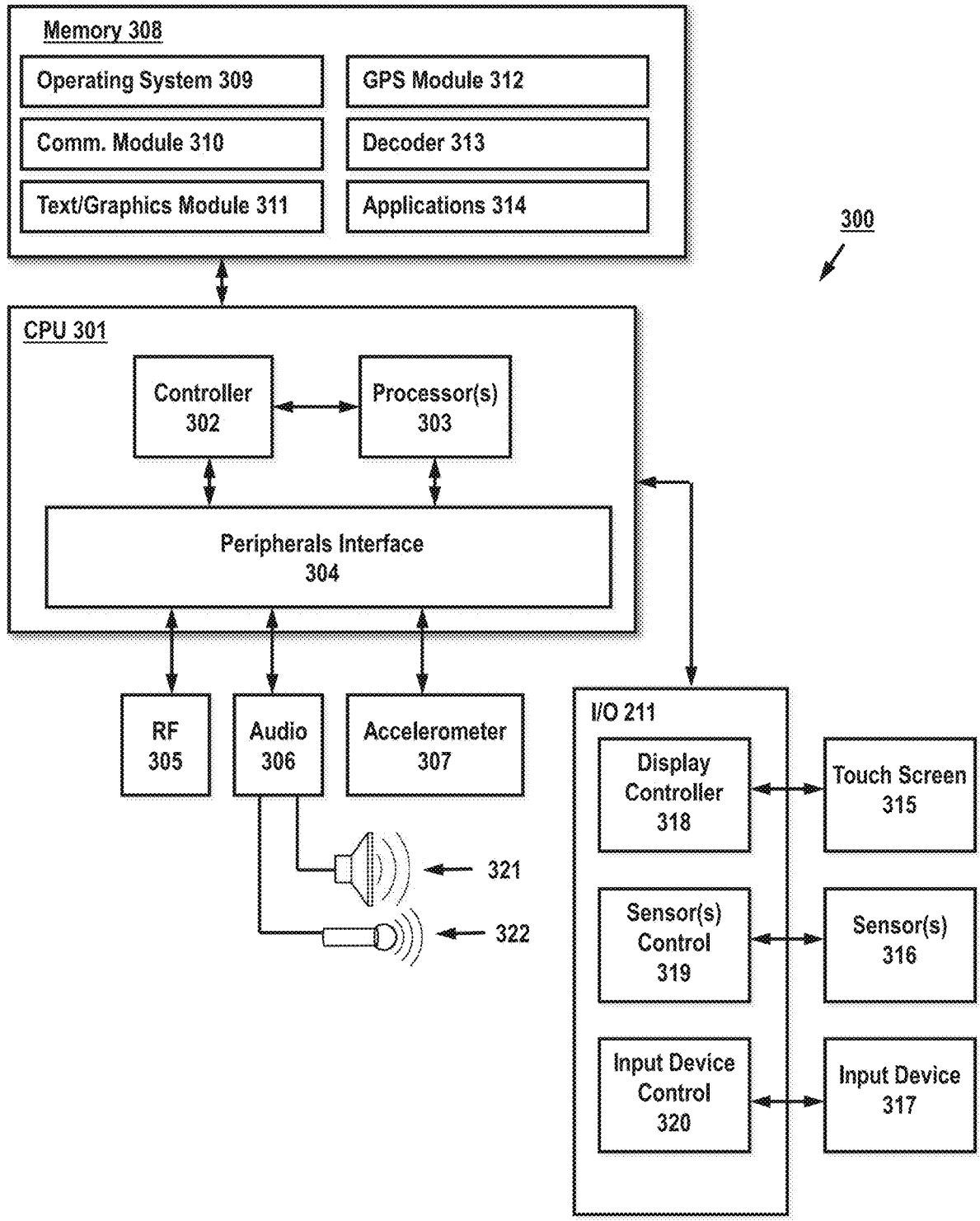
FIG. 3 schematically illustrates an operating environment for a processing device configured to perform resource processing and profile management under an illustrative embodiment.

FIG. 3 is an exemplary embodiment of a computing device 300 (such as processing devices 102-108), and may be a personal computer, smart phone, tablet computer, laptop and the like (e.g., 110-111). Device 300 may include a central processing unit (CPU) 301 (which may include one or more computer readable storage mediums), a memory controller 302, one or more processors 303, a peripherals interface 304, RF circuitry 305, audio circuitry 306, accelerometer 307, speaker 321, microphone 322, and input/output (I/O) subsystem 221 having display controller 318, control circuitry for one or more sensors 319 and input device control 320. These components may communicate over one or more communication buses or signal lines in device 300. It should be appreciated that device 300 is only one example of a portable multifunction device, and that device 300 may have more or fewer components than shown, may combine two or more components, or a may have a different configuration or arrangement of the components. The various components shown in FIG. 3 may be implemented in hardware or a combination of hardware and software, including one or more signal processing and/or application specific integrated circuits.

Memory (or storage) 308 may include high-speed random access memory (RAM) and may also include non-volatile memory, such as one or more magnetic disk storage devices, flash memory devices, or other non-volatile solid-state memory devices. Access to memory 308 by other components of the device 300, such as processor 303, and peripherals interface 304, may be controlled by the memory controller 302. Peripherals interface 304 couples the input and output peripherals of the device to the processor 303 and memory 308. The one or more processors 303 run or execute various software programs and/or sets of instructions stored in memory 308 to perform various functions for the device 300 and to process data. In some embodiments, the peripherals interface 304, processor(s) 303, decoder 313 and memory controller 302 may be implemented on a single chip, such as a chip 301. In other embodiments, they may be implemented on separate chips.

RF (radio frequency) circuitry 305 receives and sends RF signals, also known as electromagnetic signals. The RF circuitry 305 converts electrical signals to/from electromagnetic signals and communicates with communications networks and other communications devices via the electromagnetic signals. The RF circuitry 305 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 305 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

Audio circuitry 306, speaker 321, and microphone 322 provide an audio interface between a user and the device 300. Audio circuitry 306 may receive audio data from the peripherals interface 304, converts the audio data to an electrical signal, and transmits the electrical signal to speaker 321. The speaker 321 converts the electrical signal to human-audible sound waves. Audio circuitry 306 also receives electrical signals converted by the microphone 321 from sound waves, which may include utterances from a speaker. The audio circuitry 306 converts the electrical signal to audio data and transmits the audio data to the peripherals interface 304 for processing. Audio data may be retrieved from and/or transmitted to memory 308 and/or the RF circuitry 305 by peripherals interface 304. In some embodiments, audio circuitry 306 also includes a headset jack for providing an interface between the audio circuitry 306 and removable audio input/output peripherals, such as output-only headphones or a headset with both output (e.g., a headphone for one or both ears) and input (e.g., a microphone).

I/O subsystem 221 couples input/output peripherals on the device 300, such as touch screen 315, sensors 316 and other input/control devices 317, to the peripherals interface 304. The I/O subsystem 221 may include a display controller 318, sensor controllers 319, and one or more input controllers 320 for other input or control devices. The one or more input controllers 320 receive/send electrical signals from/to other input or control devices 317. The other input/control devices 317 may include physical buttons (e.g., push buttons, rocker buttons, etc.), dials, slider switches, joysticks, click wheels, and so forth. In some alternate embodiments, input controller(s) 320 may be coupled to any (or none) of the following: a keyboard, infrared port, USB port, and a pointer device such as a mouse, an up/down button for volume control of the speaker 321 and/or the microphone 322. Touch screen 315 may also be used to implement virtual or soft buttons and one or more soft keyboards.

Touch screen 315 provides an input interface and an output interface between the device and a user. Display controller 318 receives and/or sends electrical signals from/to the touch screen 315. Touch screen 315 displays visual output to the user. The visual output may include graphics, text, icons, video, and any combination thereof. In some embodiments, some or all of the visual output may correspond to user-interface objects. Touch screen 315 has a touch-sensitive surface, sensor or set of sensors that accepts input from the user based on haptic and/or tactile contact. Touch screen 315 and display controller 318 (along with any associated modules and/or sets of instructions in memory 308) detect contact (and any movement or breaking of the contact) on the touch screen 315 and converts the detected contact into interaction with user-interface objects (e.g., one or more soft keys, icons, web pages or images) that are displayed on the touch screen. In an exemplary embodiment, a point of contact between a touch screen 315 and the user corresponds to a finger of the user. Touch screen 215 may use LCD (liquid crystal display) technology, or LPD (light emitting polymer display) technology, although other display technologies may be used in other embodiments. Touch screen 315 and display controller 318 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 315.

Device 300 may also include one or more sensors 316 that may include a biometric capture device (e.g., 104). Sensors 316 may also include additional sensors, such as heart rate sensors, touch sensors, optical sensors that comprise charge-coupled device (CCD) or complementary metal-oxide semiconductor (CMOS) phototransistors. The optical sensor may capture still images or video, where the sensor is operated in conjunction with touch screen display 315. Device 300 may also include one or more accelerometers 307, which may be operatively coupled to peripherals interface 304. Alternately, the accelerometer 307 may be coupled to an input controller 320 in the I/O subsystem 221. The accelerometer is preferably configured to output accelerometer data in the x, y, and z axes.

In some illustrative embodiments, the software components stored in memory 308 may include an operating system 309, a communication module 310, a text/graphics module 311, a Global Positioning System (GPS) module 312, decoder 313 and applications 314. Operating system 309 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components. Communication module 310 facilitates communication with other devices over one or more external ports and also includes various software components for handling data received by the RF circuitry 305. An external port (e.g., Universal Serial Bus (USB), Firewire, etc.) may be provided and adapted for coupling directly to other devices or indirectly over a network (e.g., the Internet, wireless LAN, etc.).

Text/graphics module 311 includes various known software components for rendering and displaying graphics on the touch screen 315, including components for changing the intensity of graphics that are displayed. As used herein, the term "graphics" includes any object that can be displayed to a user, including without limitation text, web pages, icons (such as user-interface objects including soft keys), digital images, videos, animations and the like. Additionally, soft keyboards may be provided for entering text in various applications requiring text input. GPS module 312 determines the location of the device and provides this information for use in various applications. Applications 314 may include various modules, including resource learning logic, profile agent module, sensor software, navigation software, mapping, address books/contact list, email, instant messaging, and the like. In some illustrative embodiments, Applications 314 may communicate with sensors 316, configured as a biometric capture device.

Figure 4:
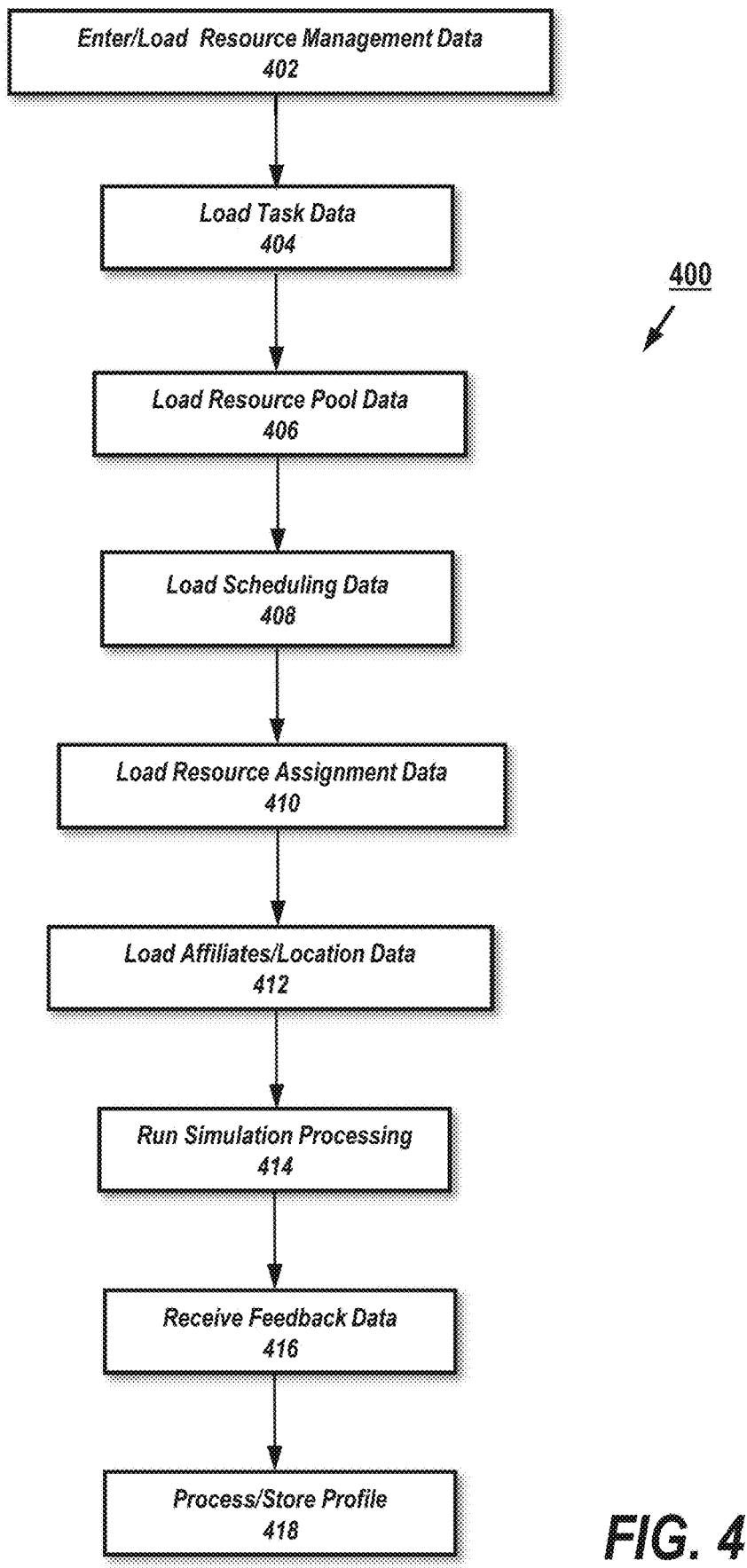
FIG. 4 shows a process for processing resource data to create a profile for resource management under an illustrative embodiment.

Turning to FIG. 4, the drawing shows a process 400 for processing resource data to create a profile for resource management under an illustrative embodiment. In this example, a computing device (e.g., 110-111) loads or enters resource management data in block 402. In block 404, the computing device may load task data that comprises tasks to be performed within the computer system (e.g., 100) and/or health care facility. In block 406, resource pool data may be loaded, which may be configured to characterize computer system, equipment and/or personnel resources available. In block 408, the computing device may be configured to load scheduling data representing computer system, equipment and/or personnel scheduling data. In block 410, the computing device may load resource assignment data that characterizes use and/or non-use of computer system, equipment and/or personnel assignments. In block 412, the computing device may load data pertaining to affiliates (e.g., nearby health care facilities) and locations. In block 414 the computing device (and/or a server) may be configured to execute simulation processing on the entered data to determine optimal resource management data via predictive/intelligence processing for use in the computer system (e.g., 100). In block 416, the computing device may receive feedback data from other processing devices (e.g., 102-108) that pertain to the present simulation and/or previous simulations. Once the feedback data is received, the computing device re-processes the simulation to reflect the feedback data, updates the simulation processing and stores the data as profile data in block 416.

The data of blocks 404-412 may be combined into the resource management data of block 402, or may be entered separately. The example of FIG. 4 illustrates an initial use of resource management software utilizing the process 400 of FIG. 4. During subsequent uses, the simulation processing of 414 may be optional, and the system (e.g., 100) would simply utilize the generated data during actual use. Also, during operation, the process 400 may loop operation, for example, in blocks 414-418, wherein the resource management software runs simulation processing (414), then receives feedback data (416) and updates the profile (418), and then re-runs simulation processing using the updated profile (414), followed by feedback data (416) and updating the profile, and so on. The number of loops may be set by a predetermined parameter, such as a time period (e.g., 5:00 AM-11:00 AM), or may be determined by a variable parameter, such as the number and/or type of feedback data received during operation.

Figure 5:
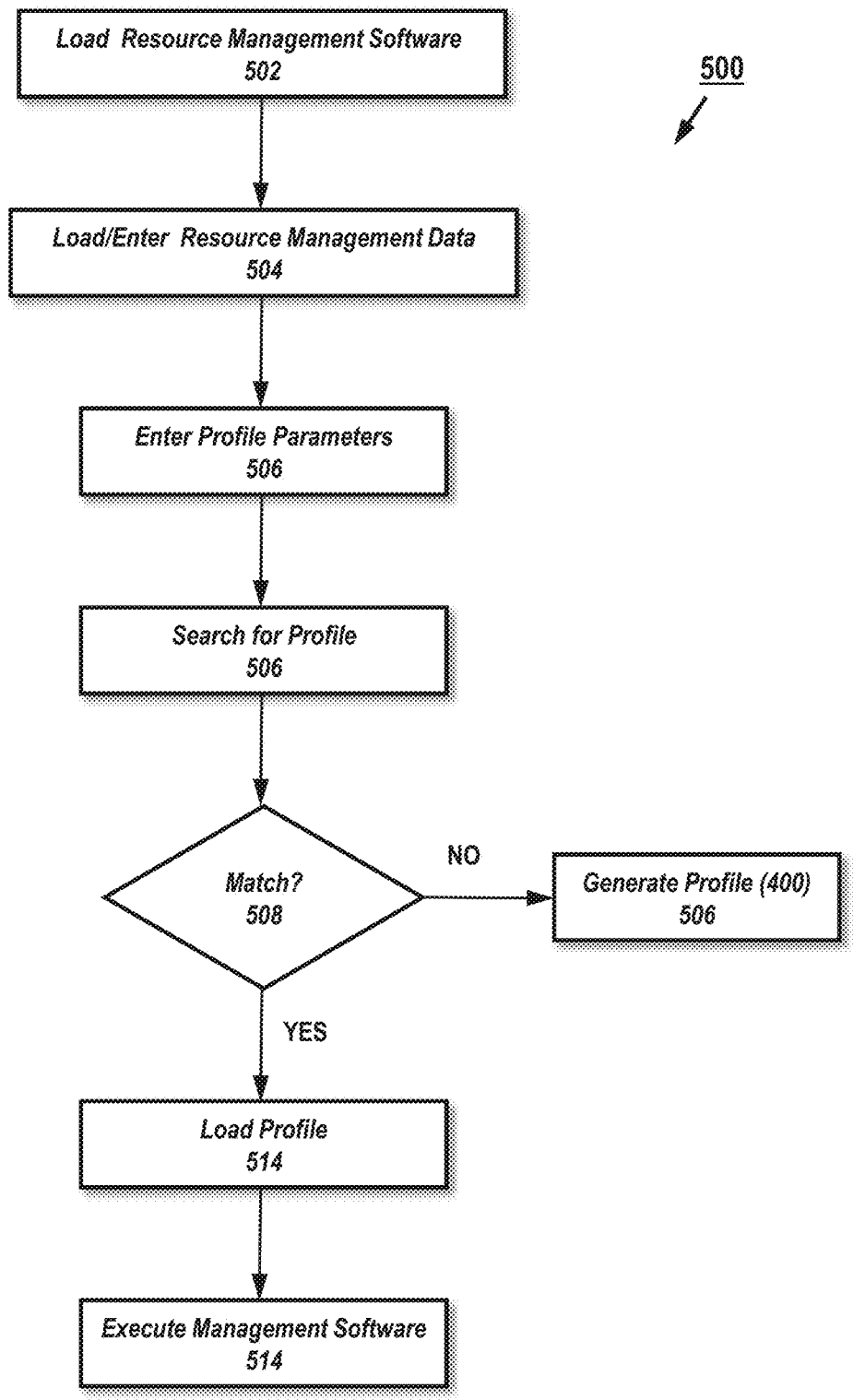
FIG. 5 shows a process for executing resource management software utilizing profile information under an illustrative embodiment.

Turning to FIG. 5, the drawing shows a process 500 for executing resource management software utilizing profile information under an illustrative embodiment. In block 502, a processing device (e.g., 110, 111) loads resource management software, and loads/receives resource management data in block 504. In block 506, the processing device may receive data for profile parameters for use in the system (e.g., 100). These profile parameters (which in some illustrative embodiments may be included as part of resource management data) may include data including, but not limited to, hospital size, location, date, medial specialty, etc. In block 506, the system, via the processing device or other device (e.g., server 116) searches a database (e.g., 118-122) to determine if there are stored profiles that match the entered parameters. In decision block 508, the system determines if there is a match to the entered parameters. Alternately or in addition, decision block 508 may determine if there is a threshold similarity between stored profiles and the entered parameters. If a match or similarity does not exit ("NO"), the process moves to block 506 where the system generates a profile, similar to the techniques discussed herein and also described in process 400 of FIG. 4. If a match or similarity exists ("YES"), the computing device receives and/or loads the matching profile in block 514. When the profile is loaded, the processing device is automatically populated with the resource management data and any associated data stored in the profile. Once loaded, the process proceeds to block 514, where the resource management software is executed, using the loaded resource management data obtained by the profile.

Figure 6:
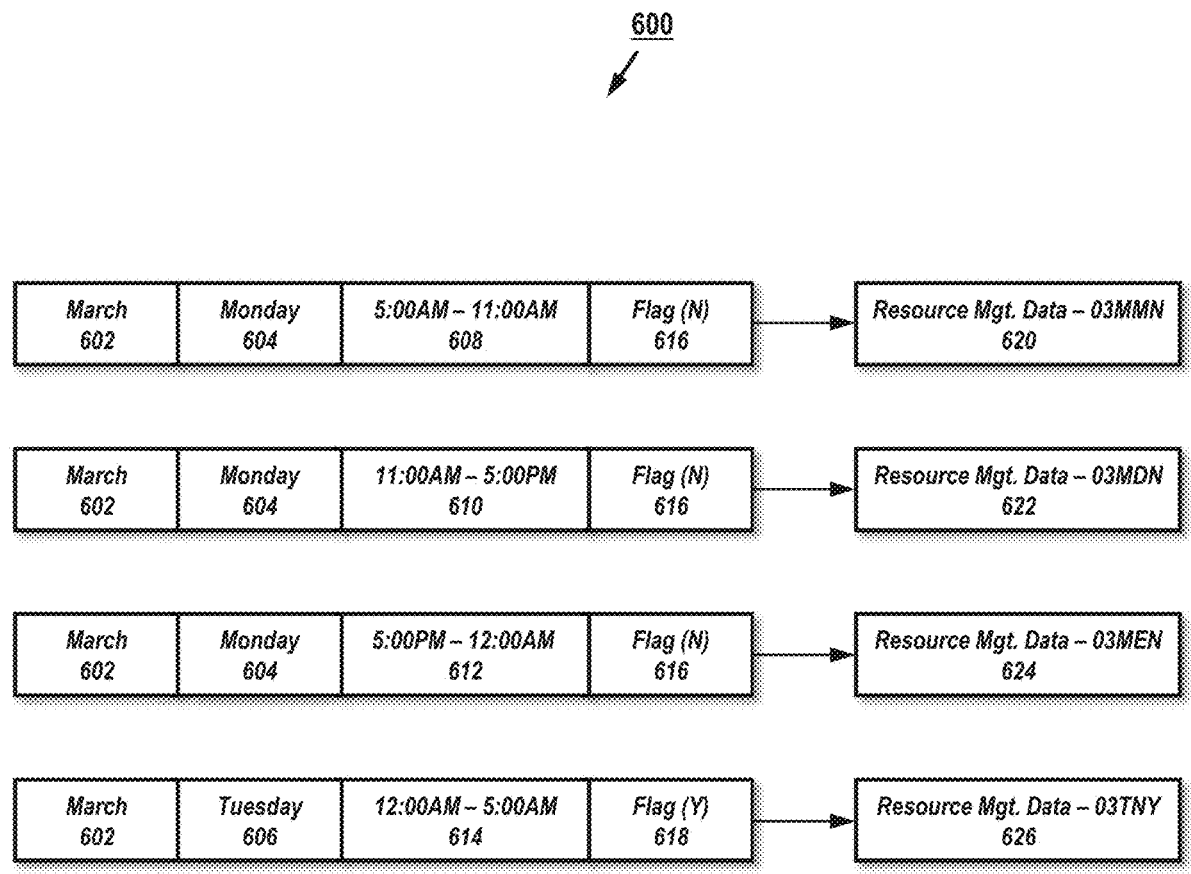
FIG. 6 shows an exemplary profile data file under an illustrative embodiment.

FIG. 6 shows an exemplary profile data file configuration 600 under an illustrative embodiment. In this example, each resource management data profile 620-626 may be configured with an identifying header, which allows the system (e.g., 100) to identify profiles in a more efficient manner. In some illustrative embodiments, the headers may be configured with chronological data, which may include a month (602), a day (604-606), a time period (608-614), as well as a flag (616-618) that may be utilized to identify a unique day (e.g., New Year's Eve, Black Friday, sporting event, etc.). As can be seen in the figure, the first resource management data profile 620 may include a header identifying the month (602), day (Monday; 604), a time period (5:00 AM-11:00 AM; 608), along with a flag (616), which is not set for the particular header ("N"). The header may be configured for the resource management data profile to include a format ("03MMN") that indicates the month ("03"), day ("M"—Monday), time ("M"—morning) and flag ("N"—"No"). Of course, those skilled in the art will recognize that FIG. 6 is a simplified example, and that a multitude of header formats are envisioned by the present disclosure.

As with resource data management data profile 620, resource data management data profile 622 has a similar header format ("03MDN") that includes the month ("03"), day ("M"—Monday), time ("D"—day) and flag ("N"—"No"). Similarly, resource data management data profile 624 has a format ("03MEN") that includes the month ("03"), day ("M"—Monday), time ("E"—evening) and flag ("N"—"No"), and resource data management data profile 626 has a header format ("03TNY") that includes the month ("03"), day ("T"—Tuesday), time ("N"—night) and flag ("Y"—"yes"). As mentioned previously, the flag may be used to designate an abnormal day, such as a holiday and/or event. In some illustrative embodiments, flags may be further configured to include additional designations carrying data to distinguish different flags, for example, as different holidays and/or events.

Figure 7:
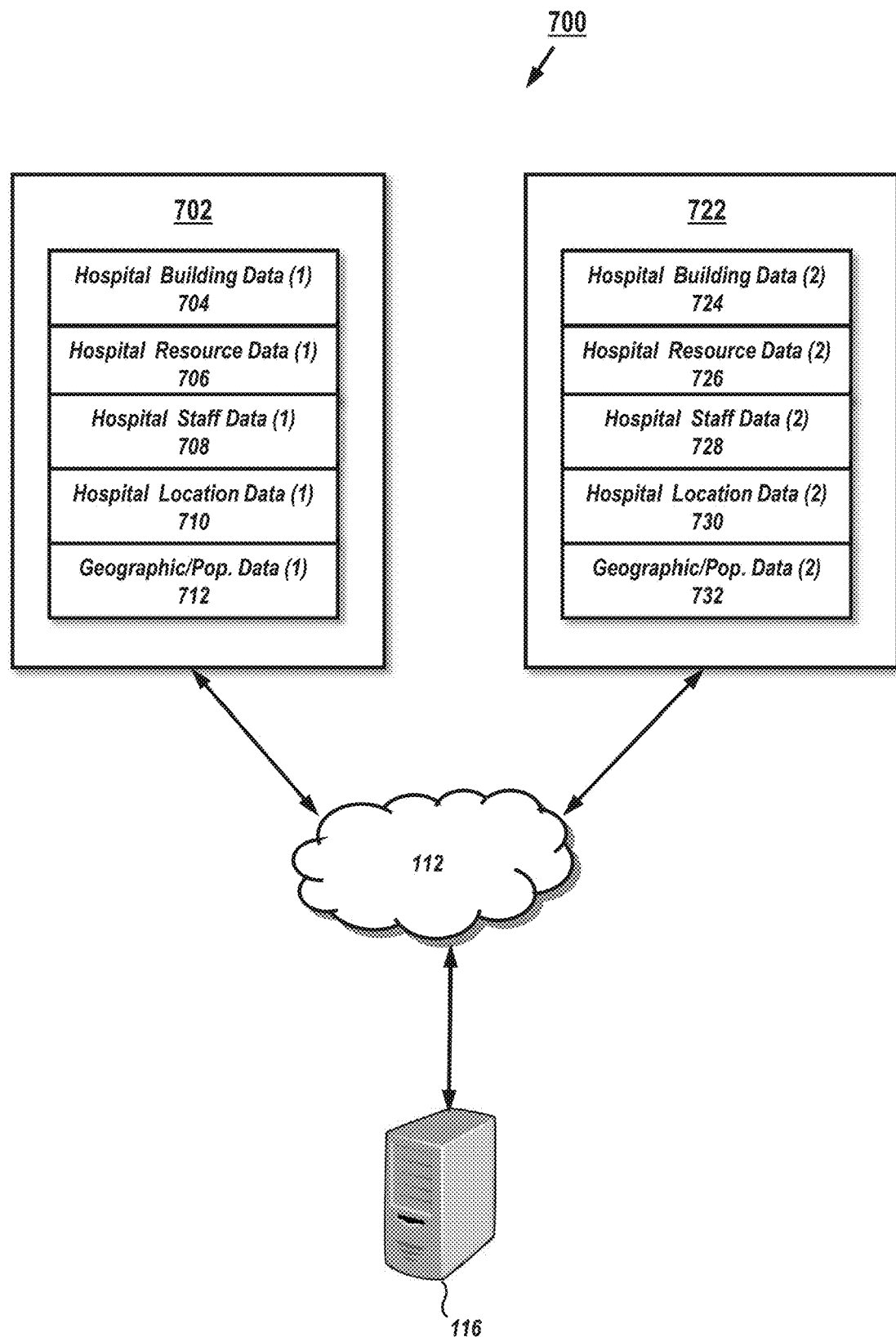
FIG. 7 shows an operating environment where two separate computer systems transmit profile data to one or more network servers for profile management processing under an illustrative embodiment.

FIG. 7 shows an operating environment 700 where two separate computer systems transmit profile data to one or more network servers (e.g., 116) for profile management processing under an illustrative embodiment. In this example, profiles 702 and 722 may be provided by two separate computer system within a larger computer system (e.g., 100). As discussed above, a first profile ("(1)") may include, but is not limited to, hospital building data 704, hospital resource data 706, hospital staff data, hospital location data 710 and/or geographic and/or population data 712 associated with the geographic location. In some illustrative embodiments, each of the data 704-712 may be provided in code form ("e.g., LB68G44 42866"), where the code is translated in the server 116 (e.g., via system profile manager 230) into usable data for system processing. In some illustrative embodiments, each of the data 704-712 may be provided via a data interface (e.g., dialog box, drop-down menu, etc.) and/or narrative text, where the text may be parsed to extract usable data. In some illustrative embodiments, each of data 704-712 may respectively utilize some combination of codes, data interfaces and/or narrative text. Of course, those skilled in the art will recognize that other techniques known in the art may be used for the data input.

Hospital building data 704 may include, but is not limited to, data relating to building size, type, layout, budget, etc. that describes the hospital building's physical and/or operational characteristics. Hospital resource data 706 may include, but is not limited to, equipment, drug treatments, inventories, etc. that describe the hospital's physical resources for treating patients, illnesses, ailments, etc. Hospital staff data 708 may include, but is not limited to, staff specialties, expertise, headcounts, headcounts-per-specialty, schedules, vacations, etc. Hospital location data 710 includes data relating to the geographical location of the hospital, and may also include locations of nearby hospitals in absolute terms and/or locations of nearby, similarly-situated hospitals, clinics, etc. Geographic and/or population data 712 may include, but is not limited to, statistical data representing the geographic area and/or the people residing in the geographic area. This data may include, but is not limited to, ethnic/racial/gender-based statistical data, income levels, crime levels, economic data, etc.

As mentioned above, second ("(2)") profile data 722 may be provided by a separate computer system from a different hospital, and may be configured similarly to profile data 702, discussed above. Accordingly, data 724-732 of the second profile data 722 may be configured similarly to first profile data 704-712, respectively, and contain the specific data pertaining to the different hospital associated with profile 722. If course, those skilled in the art will recognize that profiles 702 and 722 may contain additional data, or may contain less data than that depicted in the example of FIG. 7. Additionally, profiles 702 and 722 do not need to share exact data types relative to each other under certain illustrative embodiments. As can be seen in the figure, profiles 702 and 722 are transmitted to the network 112 and subsequently to server 116 for processing.

Figure 8:
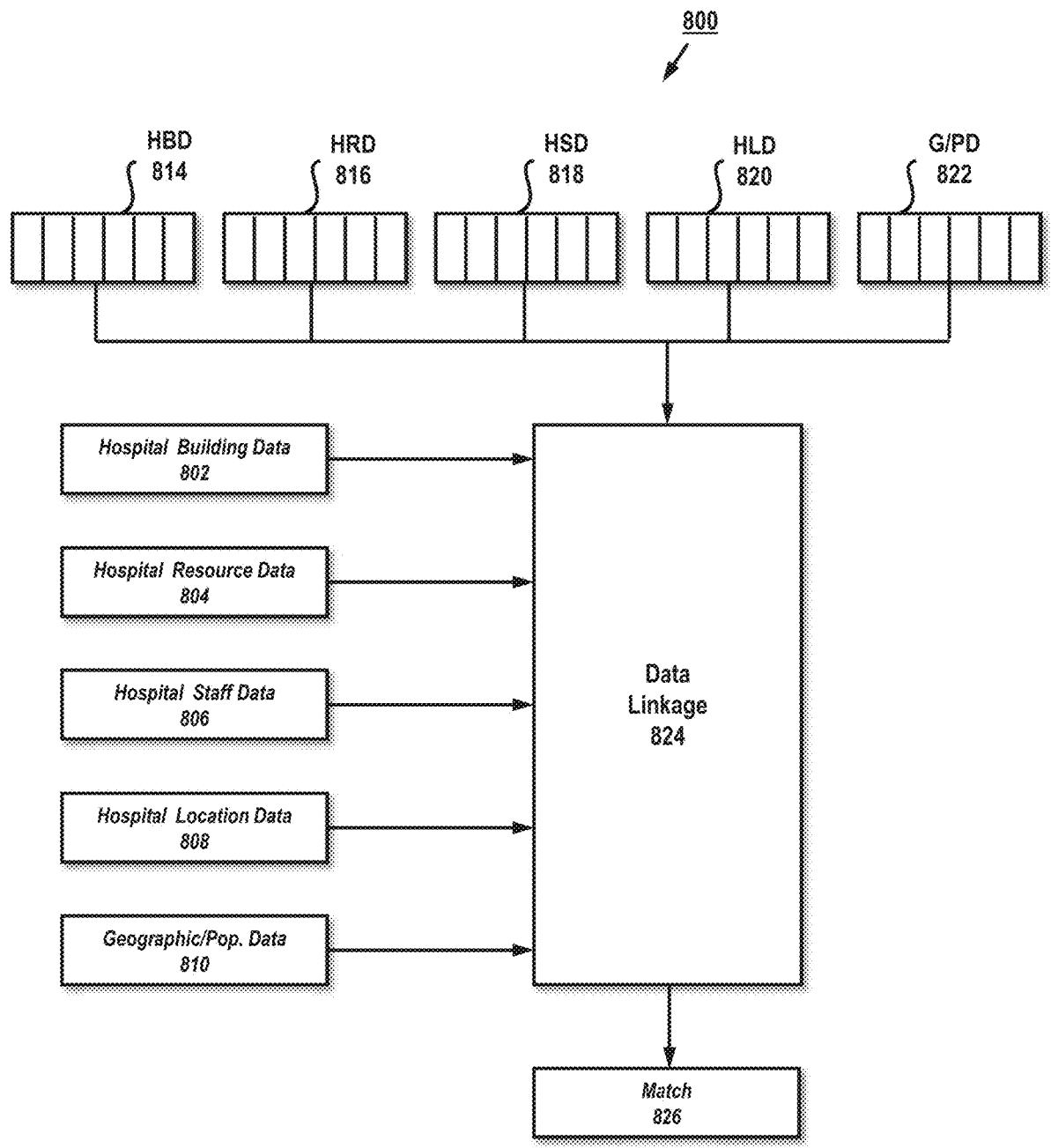
FIG. 8 shows an operating environment for a computer system that processes profile data and performs data matching processing to determine profile matches for providing resource management data under an illustrative embodiment.

FIG. 8 shows an operating environment 800 for a computer system (e.g., 100) that processes profile data and performs data matching processing to determine profile matches for providing resource management data under an illustrative embodiment. In this example, hospital building data 802. hospital resource data 804, hospital staff data 806, hospital location data 808 and geographic/population data 810 are transmitted and entered into data linkage module 824. Each of data 802-810 may be part of a profile, such as profile 702, and correspond to data 704-712, discussed above in connection with FIG. 7. In some illustrative embodiments. data linkage module 824 may be incorporated as part of the system profile manager 230. In some illustrative embodiment, each of data 802-810 are extracted and processed separately from a profile. In an alternative embodiment, some of data 802-810 may be combined for processing in data linkage module 824, depending on the specific data configuration.

Data linkage module 824 is preferably configured with a suitable data matching algorithm, depending on the application. The data matching algorithm may be either deterministic or probabilistic. In deterministic matching, elements of each data item (802-810) may be compared (e.g., via 814-822) to determine a match or an exact comparison that is used between fields. In some cases, deterministic matching is generally not preferred, since a certain field may not provide a reliable match between records. This is where probabilistic, or fuzzy, matching may be utilized in some illustrative embodiments. In probabilistic matching, several field values are compared between two records and each field may be assigned a weight that indicates how closely the two field values match (826). The sum of the individual fields weights indicates the likelihood of a match between two records.

Data linkage module 824 is coupled to a storage or database (e.g., 224, 118-122) that contains pluralities of stored data sets relating to hospital building data (HBD) 814, hospital resource data (HRD) 816, hospital staff data (HSD) 818, hospital location data (HLD) 820 and geographic/population (G/PD) data 822. This data (814-822) may be provided from other hospital computer systems in the network (e.g., 100), and/or may be provided as a baseline data set for processing. As data linkage module 824 receives hospital building data 802, it processes this data to link it to one or more elements in HBD 814. Similarly, hospital resource data 804 is processed to determine a linkage to one or more elements in HRD 816, hospital staff data 806 is processed to determine linkage to one or more elements in HSD 818, hospital location data 808 is processed to determine linkage to one or more elements in HLD 820, and geographic/population data 810 is processed to determine linkage to one or more elements in G/PD 822.

In some illustrative embodiments, data linkage module 824 may assign match/non-match weights to identifiers by means of two probabilities called u and m. The u probability may be configured as the probability that an identifier in two non-matching records will agree purely by chance. For example, the u probability for a month value (where there are twelve values that are approximately uniformly distributed) is $1/12 \approx 0.083$. Identifiers with values that are not uniformly distributed will have different u probabilities for different values (possibly including missing values). The m probability may be configured as the probability that an identifier in matching pairs will agree (or be sufficiently similar, such as strings with low Jaro-Winkler or Levenshtein distance). Ideally, this value would be 1.0 in the case of a perfect match. However, given that perfect matches are rare, the value may be estimated by the data linkage module 824. his estimation may be done based on prior knowledge of the data sets, by manually identifying a large number of matching and non-matching pairs to "train" the probabilistic record linkage algorithm, or by iteratively running the algorithm to obtain closer estimations of the m probability.

The same calculations may be done for all other identifiers under consideration to find their match/non-match weights. Then, every identifier of one record may be compared with the corresponding identifier of another record to compute the total weight of the pair. The match weight may be added to the running total whenever a pair of identifiers agree, while the non-match weight is added (i.e. the running total decreases) whenever the pair of identifiers disagrees. The resulting total weight is then compared to the aforementioned thresholds to determine whether the pair should be linked, non-linked, or set aside for special consideration (e.g. manual validation). Examples of suitable algorithms for use in data linkage module 824 include, but are not limited to, Bayesian algorithms, neural networks, perceptron, logical regression, and the like.

The match/non-match thresholds for data linkage module 824 may be modified, according to the needs and specific applications, by obtaining a suitable sensitivity (e.g., the proportion of truly matching records that are linked by the algorithm) and positive predictive value (or precision, the proportion of records linked by the algorithm that truly do match). Various manual and automated methods may be utilized to predict the best thresholds, and data linkage module 824 may be configured with built-in tools to assist finding the most acceptable values. In some illustrative embodiments, blocking techniques may be used to improve efficiency. Blocking may be advantageous in certain applications as it may operate to restrict comparisons to just those records for which one or more particularly discriminating identifiers agree, which has the effect of increasing the positive predictive value (precision) at the expense of sensitivity (recall).

As the processing in data linkage module 824 is performed, each of data 802-810 is matched to each respective stored data in 814-822 to determine individual matches to each. The data linkage module 824 may then execute a mathematical function on the data matches collectively to determine which one or more hospitals that provided their respective data 814-822 is a best match. The mathematical function may be a simple average or median function of the matched data, but preferably includes statistical normalization techniques, and may further include probabilistic processing as described herein. Once the processing is completed, data linkage module 824 identifies the one or more matching hospitals as a matching output 826. Once a hospital match is determined in 824, the system (e.g., 100) may load the associated resource management data and transmit it to the hospital that provided the original profile (e.g., 702). In the event that a plurality of matches are returned in 824, the system may perform additional processing to resolve the plurality of matches down to a single match.

Figure 9A:
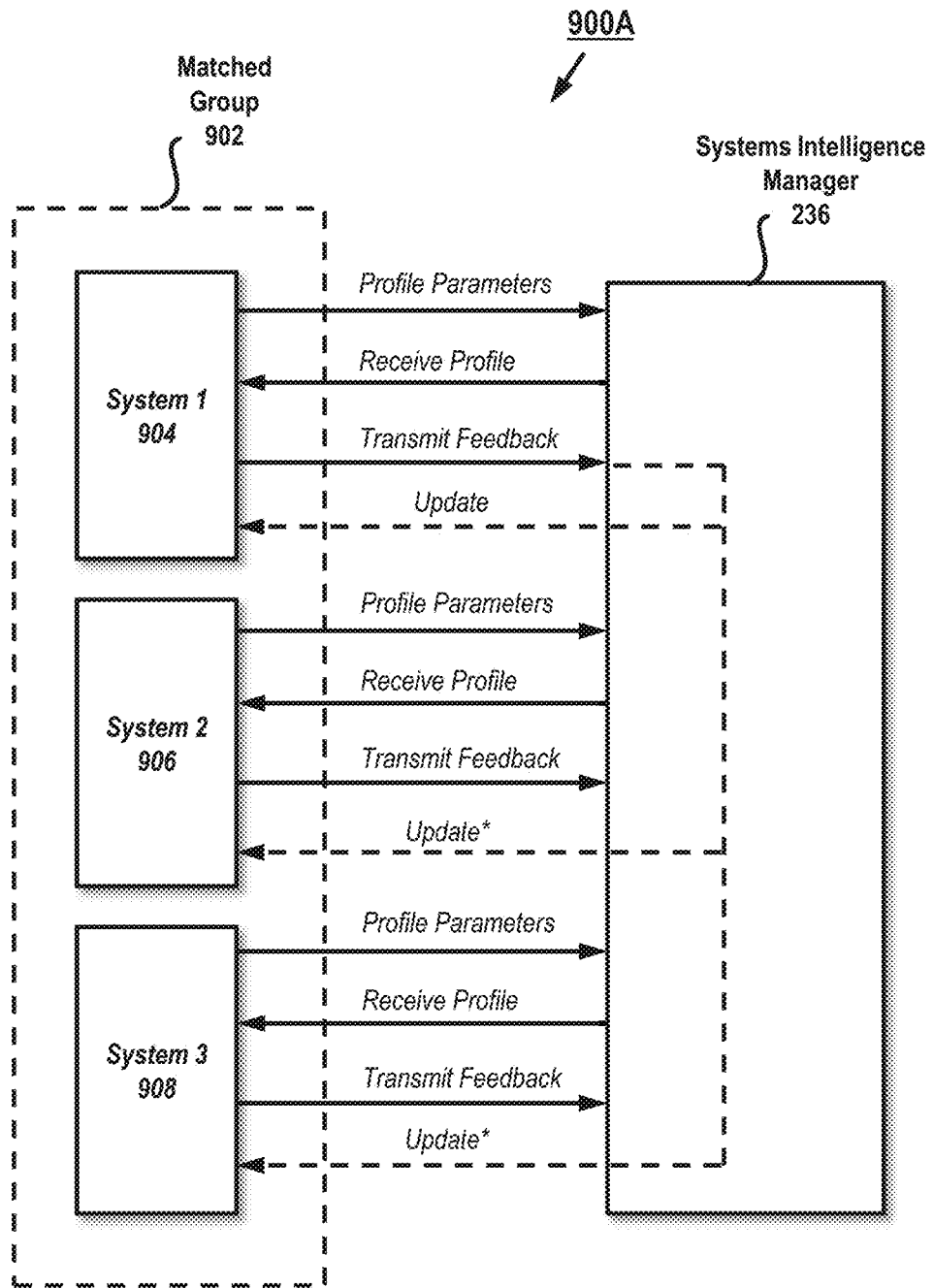
FIG. 9A shows an operating environment for a matched groups of computer systems interacting with a systems intelligence manager for providing a single feedback from one of the systems on profiled resource management data to receive updates to the resource management data under an illustrative embodiment.

FIG. 9A shows an operating environment 900A for a matched groups of computer systems (902) interacting with a systems intelligence manager 236 for providing a single feedback from one of the systems on profiled resource management data to receive updates to the resource management data under an illustrative embodiment. In the example of FIG. 9A, the figure shows a configuration where computer systems 904, 906 and 908 each provide profile parameters as discussed herein for matching, and receive a matched profile in return as result of the processing (see FIGS. 7-8). In this example, each of the computer systems 904, 906 and 908 receive a matching (i.e., substantially same) profile, which allows the system (e.g., via systems intelligence manager 236 and/or system profile manager 230) to group computer systems 904, 906 and 908 as a matched group 902, since they are operating under a substantially same profile.

As discussed herein, each of computer systems 904, 906 and 908 load resource management data associated with the received profile, and begin operation of their respective resource management software operating independently on each system (904-908). During operation, each of the computer systems 904, 906 and 908 provide feedback data to the systems intelligence manager module 236 as shown in the figure. The feedback data may be any data associated with the performance of the resource management software on each respective computer system. In some illustrative embodiments, the feedback data may be provided via an interface from the resource management software, and may include generalized feedback indicating effectiveness of one or more of the loaded resource management data (e.g., bed assignments, score 1-10; current capacity percentage, etc.). In some illustrative embodiments, the feedback, alternately or in addition, may include specific feedback indicating effectiveness of the loaded resource management data (e.g., number of excess or shortage of staff, specific utilization of equipment, etc.).

In some illustrative embodiments, systems intelligence manager module 236 is configured with threshold values that are specific to the transmitted profile and associated resource management data profiles. If one or more of the feedback data relating to an associated feature of the resource management data meets or exceeds the threshold, the systems intelligence manager module 236 provides updated resource management data relating to the feature to the computer system that provided the threshold-exceeding feedback. For example, if a computer system associated with a first hospital provides feedback indicating that staffing values are not keeping up with capacity, the systems intelligence manager may re-process the predictive/intelligence data to adjust and update the staffing requirement data of the resource management data, and provide the update back to the computer system of the first hospital. Alternately and/or in addition, the systems intelligence manager 234 may know from feedback provided by a computer system associated with a nearby second hospital, that the hospital is over-staffed at the time the feedback from the first hospital is received. In this case, the systems intelligence manager 234 may update the predictive/intelligence data to provide an update to the resource management data instructing the first hospital to increase referrals of incoming patients to the second hospital. At the same time, the systems intelligence manager 234 may update the predictive data to provide updated resource management data to the second hospital to decrease staffing for future times.

In some illustrative embodiments, the systems intelligence data includes messaging that is preferably sent contemporaneously with the updated resource management data. The messaging should be configured to inform the receiving computer system of the updates being provided. In some illustrative embodiments, the systems intelligence manager 234 may generate multiple instances of predictive/intelligence data that provide multiple, different solutions to a problem identified in the feedback data. In this case, the systems intelligence manager 234 may provide each of the updated resource management data related to each of the multiple instances of the predictive/intelligence data, along with messaging identifying each of the updated resource management data options. The messaging may include executable data allowing the computer system to select the option that the staff perceive as the best option under the circumstances. In some illustrative embodiments, the selection may be transmitted back to the systems intelligence manager 234 as further feedback that may be used to further improve the resource management data updates in the future.

Continuing with the example of FIG. 9A, computer systems 904, 906 and 908 provide feedback to the systems intelligence manager 234 as shown in the figure. In this example, the feedback data provided by computer systems 906 and 908 does not meet or exceed threshold requirements. However, the feedback from computer system 904 does meet or exceed one or more threshold requirements, which results in the systems intelligence manager module 234 providing updated resource management data back to computer system 904. Since computer systems 904, 906 and 908 are part of a matched group, the systems intelligence manager 234 provides provisional updated resource management data (designated as "update*") to systems 906 and 908. The provisional update may include additional messaging indicating that at least one other hospital of the matched group 902 is experiencing problems with a specific feature of the resource management data, and that an update is available. Each of the computer systems 906 and 908 may be given the option to accept or reject the updated resource management data. If accepted, the respective updates are loaded into the computer system and executed in the resource management software. If rejected, the update may be discarded, or alternately stored for future consideration. The acceptance/rejection of the updates may then be provided as feedback data back to the systems intelligence manager module 234.

It should be appreciated by those skilled in the art that the feedback data may be utilized by the systems intelligence manager module 234 to continue with predictive/intelligence processing to create sub-groups from the matched groups 902. For example, if computer system 908 continues to provide feedback data over time that is different or anomalous from the feedback data of computer systems 904, 906, it may be designated as a separate sub-group of the matched group 902. In such a case, computer system 908 may exclusively receive, or not receive, certain updates that are automatically provided to systems 904 and 906. This configuration would advantageously save bandwidth on the computer system (e.g., 100) and save resources on the computer system 908 by not excessively initiating updates that may not be required.

Figure 9B:
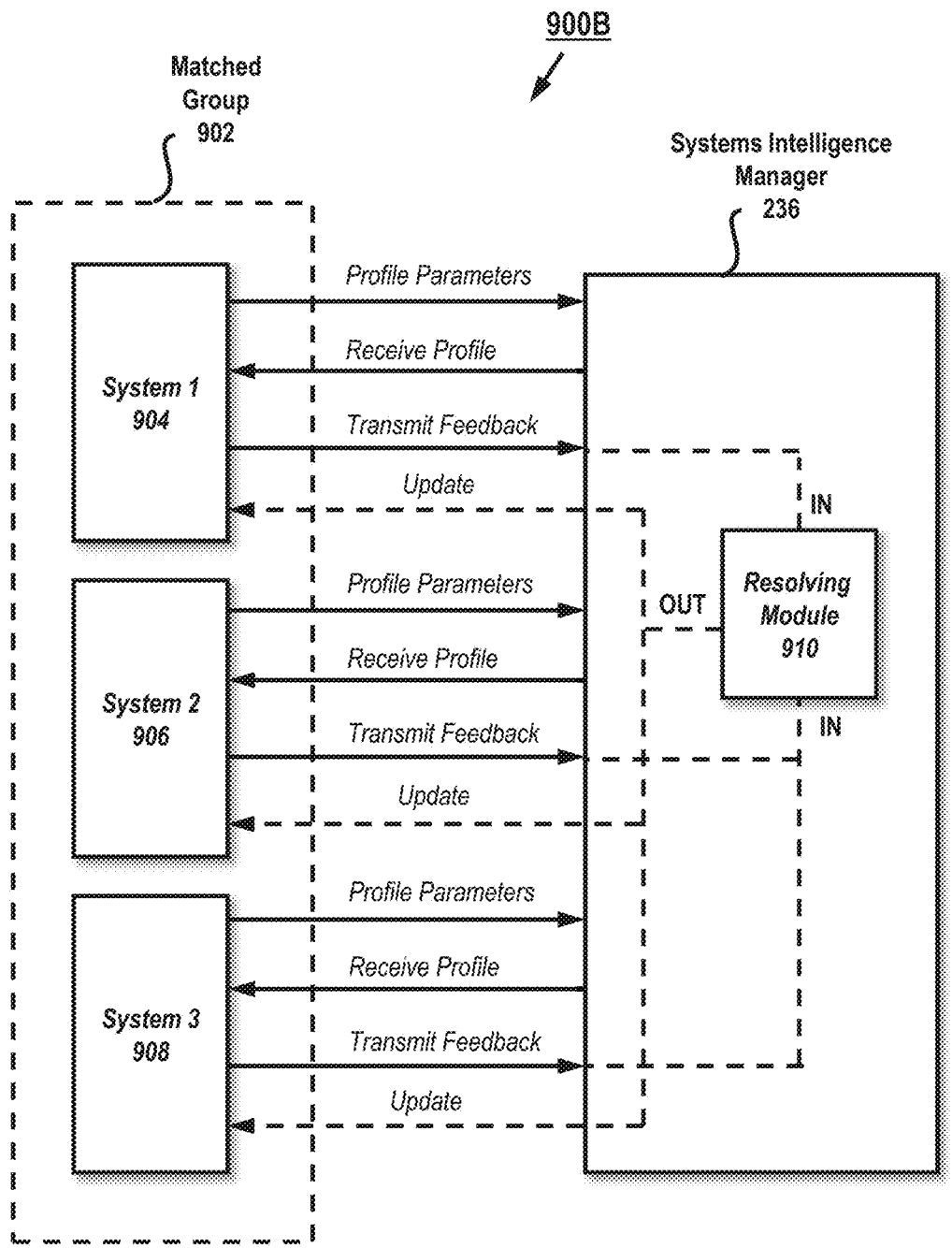
FIG. 9B shows an operating environment for a matched groups of computer systems interacting with a systems intelligence manager for providing feedback from multiple computer systems on profiled resource management data to receive updates to the resource management data via a resolving module under an illustrative embodiment.

FIG. 9B shows an operating environment 900B for a matched groups of computer systems 902 interacting with a systems intelligence manager module 234 for providing feedback from multiple computer systems on profiled resource management data to receive updates to the resource management data via a resolving module under an illustrative embodiment. In this example, the system 900B is similar to system 900A illustrated in FIG. 9A, except that systems intelligence manager 234 additionally comprises a resolving module 910, which is configured to resolve data from multiple feedbacks received from computer systems 904, 906 and 908. The resolving module 910 may be configured as a separate module, or may be integrated into the systems intelligence manager module 234.

In the example of FIG. 9B, all three computer systems 904, 906 and 908 are providing feedback during operation of resource management software on each respective system, utilizing the resource management data received from the profile match provided previously, as discussed herein. Each of the feedback data from computer systems 904, 906 and 908 are provided to resolving module 910, which processes and analyzes the feedback data to determine an optimal update to provide back to the computer systems. Here, it may be assumed that at least two of the computer systems 904, 906 and 908 are providing feedback that is different with respect to at least one resource management data feature. Here, each of the feedback data received from computer systems 904, 906 and 908 are input ("IN") to the resolving module 910 that may be configured to perform a mathematical function on the received feedback inputs. As described elsewhere herein, the mathematical function may be a simple average or median function of the feedback data, but preferably includes statistical normalization techniques, and may further include probabilistic processing as described herein.

Once processed, the resolving module 910 outputs ("OUT") updated resource management data to each of the computer systems 904, 906 and 908 as shown in the figure. In some illustrative embodiments, the updated resource management data may be the same for each computer system 904, 906 and 908 and represent normalized values for the updates. In some illustrative embodiments, the updated resource management data may be different for at least one of the computer systems 904, 906 and 908.

Those skilled in the art will appreciate that the present disclosure provides elegant and efficient technologies and techniques that allow system users to execute resource management software while using fewer computer resources and network resources during operation. Additionally, utilizing the resource management profiles, a resource management computer system may utilize the data of other, similarly situated systems, which also saves computer resources, while also obviating the need to run extensive simulation (i.e., predictive/learning processing) prior to a first use of the software, or prior to a resource management cycle (e.g., time period). Furthermore, by providing profile headers and/or tagging specific profiles, resource management systems may quickly search for profiles that may be useful for specific uses and/or circumstances. Moreover, the use of feedback data for predictive processing allows the computer system to provide more accurate data that may be utilized by the user(s).

The figures and descriptions provided herein may have been simplified to illustrate aspects that are relevant for a clear understanding of the herein described devices, structures, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide this thorough understanding of embodiments of the present disclosure. Nevertheless, it will be apparent to those skilled in the art that specific disclosed details need not be employed, and that exemplary embodiments may be embodied in different forms. As such, the exemplary embodiments should not be construed to limit the scope of the disclosure. In some exemplary embodiments, well-known processes, well-known device structures, and well-known technologies may not be described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

The disclosed embodiments may be implemented, in some cases, in hardware, firmware, software, or any tangibly-embodied combination thereof. It is understood by those skilled in the art that the present disclosure do The disclosed embodiments may also be implemented as instructions carried by or stored on one or more non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A resource management system for optimizing and distributing predictively processed data in a medical software application of a computer network, comprising:
   a memory configured to store profile data of a plurality of computer systems of the computer network associated with different remote health care facilities, and profile data comprising (i) data relating to operational characteristics of a first remote health care facility associated with a first computer system of the computer network, wherein the data comprises a header format indicating chronological operating characteristics, and (ii) resource management data associated with the profile data, wherein the resource management data comprises predictively pre-processed data for optimizing the data relating to the operational characteristics, and utilizing the header format, associated with the first remote health care facility;

a processing apparatus, operatively coupled to the memory, wherein the processing apparatus is configured to probabilistically group the plurality of computer systems of the computer network associated with different remote health care facilities matching the stored profile data of the first computer system, based on linked characteristics of each grouped health care facility to the first remote health care facility associated with the first computer system; and a communications interface, operatively coupled to the processing apparatus, wherein the communications interface is configured to transmit the resource management data to the grouped plurality of computer systems on the network and receive respective feedback data from each of the grouped plurality of computer systems in response to the resource management data, wherein one or more of the received feedback data comprises an indication that one or more features of a respective execution of the medical software application for a current operational cycle includes an out-of-threshold condition relative to the capabilities and capacities, wherein the processing apparatus is configured to predictively process the resource management data via simulation based on a resource model and the feedback data to generate updated resource management data for further optimizing operational capability and capacity data and addressing the out-of-threshold condition for a future operational cycle of the medical software application, and wherein the processor is configured to transmit the updated resource management data to the at least one of the computer systems indicating the out-of-threshold condition, the updated resource management data being configured to replace at least a portion of the resource management data of the at least one of the computer systems, and for loading and execution in the medical software application of the at least one of the computer systems.

2. The resource management system of claim 1, wherein the processor is configured to apply a resource model to perform the predictive processing.

3. The resource management system of claim 2, wherein the resource model comprises one of a decision tree hierarchical structure, an Agent-Based Model (ABM), and a fuzzy logic model.

4. The resource management system of claim 1, wherein the format header comprises chronological data associated with the resource management data for a configured time period, wherein the chronological data comprises flags to indicate different abnormal chronological conditions.

5. The resource management system of claim 4, wherein the processor is configured to re-group the plurality of computer systems of the computer network associated with different health care facilities matching the stored profile data of the first computer system based on the chronological data.

6. The resource management system of claim 1, wherein the processor is configured to transmit the updated resource management data to at least another one of the computer systems based on feedback data not indicating the out-of-threshold condition.

7. The resource management system of claim 5, wherein the updated resource management data transmitted to at least another one of the computer systems based on feedback data not indicating the out-of-threshold condition comprises messaging indicating out-of-threshold conditions received from the feedback.

8. A method for optimizing and distributing predictively processed data in a medical software application of a resource management system operating on a computer network, comprising:

storing, on a memory, profile data of a plurality of computer systems of the computer network associated with different health care facilities, and profile data comprising (i) data relating to operational characteristics of a first remote health care facility associated with a first computer system of the computer network, wherein the data comprises a header format indicating chronological operating characteristics, and (ii) resource management data associated with the profile data, wherein the resource management data comprises predictively pre-processed data for optimizing operational capability and capacity data, and utilizing the header format, associated with the first remote health care facility;

probabilistically grouping, via a processing apparatus, a plurality of computer systems of the computer network associated with different health care facilities matching the stored profile data of the first computer system, based on linked characteristics of each grouped health care facility to the remote first health care facility associated with the first computer system;

transmitting, via a communications interface, the resource management data to the grouped plurality of computer systems on the network;

receiving, via the communications interface, respective feedback data from each of the grouped plurality of computer systems in response to the resource management data, wherein one or more of the received feedback data comprises an indication that one or more features of a respective execution of the medical software application for a current operational cycle includes an out-of-threshold condition relative to the capabilities and capacities;

predictively processing, via the processing apparatus, the resource management data via simulation, based on the feedback data to generate updated resource management data for further optimizing operational capability and capacity data and addressing the out-of-threshold condition for a future operational cycle of the medical software application; and transmitting the updated resource management data to the at least one of the computer systems indicating the out-of-threshold condition, the updated resource management data being configured to replace at least a portion of the resource management data pf the at least one of the computer systems, and for loading and execution of further optimized operational capability and capacity data in the medical software application of the at least one of the computer systems.

9. The method of claim 8, wherein predictively processing the resource management data via simulation comprises applying a resource model to perform the predictive processing.

10. The method of claim 9, wherein the resource model comprises one of a decision tree hierarchical structure, an Agent-Based Model (ABM), and a fuzzy logic model.

11. The method of claim 8, wherein the format header comprises chronological data associated with the resource management data for a configured time period, wherein the chronological data comprises flags to indicate different abnormal chronological conditions.

12. The method of claim 11, further comprising re-grouping the plurality of computer systems of the computer network associated with different health care facilities matching the stored profile data of the first computer system based on the chronological data.

13. The method of claim 8, wherein transmitting the updated resource management data comprises transmitting the updated resource management data to at least another one of the computer systems based on feedback data not indicating the out-of-threshold condition.

14. The method of claim 13, wherein the updated resource management data transmitted to at least another one of the computer systems based on feedback data not indicating the out-of-threshold condition comprises messaging indicating out-of-threshold conditions received from the feedback.

15. A resource management system for optimizing and distributing predictively processed data in a medical software application of a computer network, comprising:
- a memory configured to store profile data of a plurality of computer systems of the computer network associated with different health care facilities, and first profile data comprising (i) data relating to operational characteristics of a first remote health care facility associated with a first computer system of the computer network, wherein the data comprises a header format indicating chronological operating characteristics, and (ii) resource management data associated with the first profile data, wherein the resource management data comprises predictively pre-processed data for optimizing operational capability and capacity data, utilizing the header format, associated with the first remote health care facility, and;
- a processing apparatus, operatively coupled to the memory, wherein the processing apparatus is configured to probabilistically group the plurality of computer systems of the computer network associated with different health care facilities matching the stored first profile data of the first computer system, based on linked characteristics of each grouped health care facility to the first remote health care facility associated with the first computer system; and
- a communications interface, operatively coupled to the processing apparatus, wherein the communications interface is configured to transmit the resource management data to the grouped plurality of computer systems on the network and receive respective feedback data from each of the grouped plurality of computer systems in response to the resource management data, wherein one or more of the received feedback data comprises an indication that one or more features of a respective execution of the medical software application for a current operational cycle includes an out-of-threshold condition relative to the resource management data,
- wherein the processing apparatus is configured to predictively process the resource management data via simulation based on the feedback data to generate updated resource management data for further optimizing operational capability and capacity data and addressing the out-of-threshold condition for a future operational cycle of the medical software application,
- wherein the processor is configured to transmit the updated resource management data to the at least one of the computer systems indicating the out-of-threshold condition, the updated resource management data being configured to replace at least a portion of the resource management data of the at least one of the computer systems, and wherein the updated resource management data is configured to be loaded and executed for the future operational cycle,
- and wherein the processor is configured to transmit the updated resource management data to at least one of the other computer systems not indicating the out-of-threshold condition, wherein the updated resource management data is configured provisionally to be selectively loaded and executed for the future operational cycle.

16. The resource management system of claim 15, wherein the processor is configured to apply a resource model to perform the predictive processing, comprising one of a decision tree hierarchical structure, an Agent-Based Model (ABM), and a fuzzy logic model.

17. The resource management system of claim 15, wherein the format header comprises chronological data associated with the resource management data for a configured time period, wherein the chronological data comprises flags to indicate different abnormal chronological conditions.

18. The resource management system of claim 17, wherein the processor is configured to re-group the plurality of computer systems of the computer network associated with different health care facilities matching the stored profile data of the first computer system based on the chronological data.

19. The resource management system of claim 15, wherein the processor is configured to transmit the updated resource management data to at least another one of the computer systems based on feedback data not indicating the out-of-threshold condition.

20. The resource management system of claim 17, wherein the updated resource management data transmitted to at least another one of the computer systems based on feedback data not indicating the out-of-threshold condition comprises messaging indicating out-of-threshold conditions received from the feedback.

* * * * *